(12) United States Patent
Zank

(10) Patent No.: US 9,500,609 B1
(45) Date of Patent: Nov. 22, 2016

(54) METHOD FOR DETECTING TARGET MATERIALS USING NUCLEAR QUADRUPOLE RESONANCE

(71) Applicant: BAE Systems Information and Electronic Systems Integration Inc., Nashua, NH (US)

(72) Inventor: Paul A. Zank, Brookline, NH (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 586 days.

(21) Appl. No.: 13/975,940

(22) Filed: Aug. 26, 2013

Related U.S. Application Data

(60) Provisional application No. 61/692,840, filed on Aug. 24, 2012, provisional application No. 61/692,842, filed on Aug. 24, 2012, provisional application No. 61/692,846, filed on Aug. 24, 2012, provisional application No. 61/692,850, filed on Aug. 24, 2012.

(51) Int. Cl.
*G01N 24/08* (2006.01)
*G01R 33/44* (2006.01)

(52) U.S. Cl.
CPC ........... *G01N 24/084* (2013.01); *G01R 33/441* (2013.01)

(58) Field of Classification Search
CPC .............................. G01N 24/084; G01R 33/441
See application file for complete search history.

(56) References Cited

U.S. PATENT DOCUMENTS

| | | | |
|---|---|---|---|
| 6,194,898 B1 | 2/2001 | Magnuson et al. | |
| 8,463,557 B2 * | 6/2013 | Apostolos ............ | G01R 33/441 324/307 |
| 8,570,038 B2 * | 10/2013 | Zank ...................... | G01R 33/12 324/300 |
| 8,674,697 B2 * | 3/2014 | Apostolos ............ | G01R 33/441 324/300 |
| 8,710,837 B2 * | 4/2014 | Zank .................... | G01R 33/441 324/307 |
| 8,773,127 B2 * | 7/2014 | Apostolos ................ | G01V 3/14 324/307 |
| 8,922,211 B2 * | 12/2014 | Apostolos ............ | G01R 33/441 324/307 |
| 2003/0071619 A1 * | 4/2003 | Sauer ................... | G01R 33/441 324/307 |
| 2004/0235435 A1 * | 11/2004 | Barabash .............. | H03F 1/0205 455/104 |
| 2009/0039884 A1 | 2/2009 | Schiano | |
| 2011/0187363 A1 * | 8/2011 | Zank .................... | G01R 33/441 324/307 |
| 2012/0161771 A1 | 6/2012 | Apostolos et al. | |

FOREIGN PATENT DOCUMENTS

| | | |
|---|---|---|
| EP | 0813685 | 12/2004 |
| WO | 2011126594 | 1/2011 |
| WO | 2011152887 | 1/2011 |

* cited by examiner

*Primary Examiner* — Rodney Bonnette
(74) *Attorney, Agent, or Firm* — Sand & Sebolt, LPA; Daniel J. Long; Scott J. Asmus

(57) ABSTRACT

A method for detecting target material or explosives using Nuclear Quadrupole Resonance, comprises the steps of providing a sample material to test for a target material. The sample material is then irradiated with a first frequency from a continuous wave signal generator to create at least one sample material return frequency. A return frequency is then measured and it is determined whether the sample material contains the target material by comparing the return frequency to a known target material frequency in a library. The method allows for simultaneous irradiation of sample material and measuring the return frequency of the sample material. The method utilizes NQR to detect explosive material using a power safe for human scanning and testing.

20 Claims, 3 Drawing Sheets

METHOD FOR DETECTING TARGET MATERIALS USING NUCLEAR QUADRUPOLE RESONANCE

CROSS REFERENCE TO RELATED APPLICATIONS

This application claims the earliest benefit of U.S. Provisional Application Ser. No. 61/692,840 filed on Aug. 24, 2012; Ser. No. 61/692,842 filed on Aug. 24, 2012; Ser. No. 61/692,846 filed on Aug. 24, 2012; Ser. No. 61/692,850 filed on Aug. 24, 2012, the disclosures of which are incorporated herein by reference.

BACKGROUND OF THE INVENTION

Technical Field

The present invention relates generally to the detection of a target material contained within a sample material. More particularly, the present invention relates the detection of explosives contained in a sample material. Specifically, the present invention utilizes Nuclear Quadrupole Resonance to locate the target material so it may be evaluated and determined whether it is an explosive.

Background Information

Since the earliest days of explosive and contraband detection, people have been trying to gain advantages over their opponents. These advantages have become more desirable ever since the advent of extremely deadly explosives, and highly illegal contraband. One desirable advantage is the ability to remotely detect an explosive within a set of sample material. This sample material could be in the ground, so as to detect an explosive mine or the sample material may be separated from the ground, so as to detect an explosive bomb or contraband contained in a box.

Prior to describing the subject invention and by way of further background, in the early 1900s, not long after Einstein published his equations on thermal equilibrium, individuals realized that there were likely to be resonances at very low frequencies for atoms and molecules and that these resonances would occur because if one emits a photon of exactly the correct frequency, the material will absorb this photon, store it for some amount of time and then get rid of the absorbed energy. It is has been found that in nature the molecules which absorb such energy always fall to a lower energy state.

One of the ways for the material to emit energy is through spontaneous emission where a photon of exactly the same energy that is impinging on the material is thrown off in a random direction at random times.

The second way of getting rid of the energy absorbed by the material is through process of stimulated emission in which a photon arrives at exactly the appropriate energy, gets near the molecule, stimulates the molecule and when the molecule drops to the lower energy state it emits a photon that is exactly in phase with the original photon.

The energy that is thrown off either in spontaneous emission or stimulated emission results in a narrow spectral line. In fact, the line is generally considered to be a single line that exists at a given wavelength or frequency.

Nuclear quadrupole resonance (NQR) is a branch of radio-frequency spectroscopy (which includes the study of spectral lines). NQR has been utilized in the past to detect the presence of specific molecules, including explosives. Explosives generally involve the use of nitrogen or nitrogen bonded with other elements. When NQR was utilized in the past, it was used to detect the presence of molecules due to the molecular elements that are bonded together such that the molecules absorb energy at, for instance, as many as eight different energy levels or spectral lines. It turns out that at least three of the energy levels tend to be prominent. Although in some materials, there are upwards of all eight energy levels for one bond. If one has many bonds, there may be many dozens of spectral lines. In order to detect the presence of a molecule one usually is looking to pump energy right at the top of one of the spectral lines and look for energy coming back at the same frequency.

A further background explanation of NQR was originally published in U.S. Pat. No. 6,194,898 ('898 patent). The '898 patent explains that NQR exploits the inherent electrical properties of atomic nuclei. Nuclei with non-spherical electric charge distributions possess electric quadrupole moments. Quadrupole resonance arises from the interaction of the nuclear quadrupole moment of the nucleus with the local applied electrical field gradients produced by the surrounding atomic environment. NQR does not require an external static magnetic field as NMR does.

Any chemical elements nucleus having a spin quantum number greater than one half can exhibit quadrupolar resonance. Many substances (approximately 10,000) have been identified that exhibit quadrupolar resonance, among such nuclei being: $^7$Li, $^9$Be, $^{14}$N, $^{17}$O, $^{23}$Na, $^{27}$Al, $^{35}$Cl, $^{37}$Cl, $^{39}$K, $^{55}$Mn, $^{75}$As, $^{79}$Br, $^{81}$Br, $^{127}$I, $^{197}$Au, and $^{209}$Bi. It so happens that some of these quadrupolar nuclei are present in explosive and narcotic (i.e., contraband) materials, among them being nitrogen ($^{14}$N), chlorine ($^{35}$Cl, $^{37}$Cl), oxygen ($^{17}$O), sodium ($^{23}$Na), and potassium ($^{39}$K). The most studied quadruple nucleus for explosives and contraband detection is nitrogen.

In solid materials, electrons and atomic nuclei produce electric field gradients. These gradients modify the energy levels of any quadrupolar nuclei and hence their characteristic transition frequencies. Measurements of these frequencies or relaxation time constants, or both, can indicate not only which nuclei are present but also their chemical environment.

When an atomic quadrupolar nucleus is within an electric field gradient, variations in the local field associated with the field gradient affect different parts of the nucleus in different ways. The combined forces of these fields cause the quadrupole to experience a torque, which causes it to precess about the electric field gradient. Precessional motion generates an oscillating nuclear magnetic moment. An externally applied radio frequency (RF) magnetic field in phase with the quadrupole's precessional frequency can tip the orientation of the nucleus momentarily. The energy levels are briefly not in equilibrium, then the energy levels immediately begin to return to equilibrium. As the nuclei return to equilibrium, they produce an RF signal, known as the free induction decay (FID) or return frequency. A pick-up coil detects the signal, which is subsequently amplified by a sensitive receiver to measure its characteristics.

One distinguishing of an NQR response is the NQR relaxation times. Relaxation times are a measure of the nuclei's rate of return to the equilibrium state following disturbance by an RF irradiation pulse. Relaxation times are compound-, temperature-, and pressure-specific. Relaxation times also determine the repetition rate and timing of RF pulses required for exciting and detecting a specific NQR signal. Relaxation times from pulsed systems can be as long as eight seconds for some materials like TNT.

The '898 patent discloses a method for detecting a target substance within a class of explosives and narcotics containing quadrupolar nuclei in a specimen, said method employing the phenomenon of nuclear quadrupole resonance (NQR) in a pulsed detection system and comprising the steps of: forming a scanner having an RF Coil for a probe; entering known characteristics of NQR signals of target substances in memory in a signal processor in the detection system; providing programmed timing pulses to the detection system; inserting the specimen within the volume enclosed by the RF coil; then automatically adaptively tuning the RF coil to maximize power transfer efficiency for RF signals transmitted within the RF coil cavity; providing excitation RF pulses of a predetermined frequency to the RF coil; transmitting the RF pulses into the cavity formed by the RF coil and creating a flux field with the RF coil to which the specimen is subjected; detecting by the RF coil the NQR signals emitted by target substances within the specimen; processing the NQR signals and comparing them to known signal characteristics to determine whether the detected NQR signals indicate the presence of a target substance; and indicating whether the target substance is present in the specimen.

Problems and issues may still arise with the '898 patent, namely, with respect to the detection of explosives or other contraband. One problem is that certain non-explosive materials also contain nitrogen bonds having energy levels substantially equal or in a similar frequency range as an explosive or contraband material. An additional problem results from the RF pulses. The RF pulses require a large amount of power. The amount of power needed to operate the system of the '898 patent is 1 to 2 KW RF power amplifier for examining airline baggage for explosives. This system would be unsafe for direct human use.

Further, an issue arises where the RF pulses would require a relaxation time (the time between the broadcasted pulse signals and a receiver being able to locate a return frequency signal) in the range of about 3 to 8 seconds for detecting trinitrotoluene (TNT). This relaxation time is too long for any real world application requiring scanning of moving people. This is because the device would have to stop irradiating signals and "listen" for the NQR emission or return frequency until sample material would stop resonating prior to device sending out another pulse. Or, this problem would also arise when the pulsed system would be transmitting signals while simultaneously trying to measure or listen for the return frequency.

Another issue with pulsed NQR detection systems is there is a large dynamic range in decibels (db, the ratio between two values of a physical quantity, power and intensity [amplitude]). The dynamic range can be as large as 150 db to measure a return frequency for a target material within a sample material. For example, to locate a nitrate in a sample material, an electromagnetic pulsed signal is transmitted/broadcasted at 0 db (1 to 1 ratio) into the sample material. The expected NQR emitted signal from any nitrate would be in an expected range from about −125 db to about −150 db. This is an extremely low level of return signal strength, making it difficult to positively identify the nitrate.

A United States Patent Application Publication 2009/0039884 ('884 application), published in the name of Schiano, discloses a method of using a method of characterizing a nuclear quadrupole resonance for an analyte within a sample volume using continuous wave (CW) spectroscopy, the method being performed by a spectrometer, the method comprising: applying an excitation magnetic field having a search frequency to the sample volume; adjusting the search frequency using a blind search algorithm to detect a resonance absorption signal; and adjusting the search frequency using an extremum seeking algorithm so as to determine an extremum in the resonance absorption signal.

The '884 application is remarkable in that problems may arise with respect to searching for target material. The '884 application may still have relaxation times in the range of 3-8 seconds for target materials, such as TNT, because the '884 application does not disclose any way of suppressing the transmitted excitation signal from overdriving or jamming the receiver detection circuit. Further, it may be unsafe for human use depending on the total power irradiating the sample material.

The present invention addresses these and other issues.

SUMMARY

In one aspect, the invention may provide a method for detecting target materials using Nuclear Quadrupole Resonance (NQR), comprising the steps of: providing a sample material to test for a target material; irradiating the sample material with a continuous wave (CW) signal frequency generated by a signal generator while simultaneously measuring the sample material NQR emissions by nulling out the irradiated signal frequency utilizing a balanced bridge circuit; and determining whether the sample material contains the target material by comparing the measured emission frequency to a known target material frequency in a library.

In another aspect, the invention may provide a system and method of generating a continuous wave signal to generate an NQR response return frequency within the sample material under test. An embodiment of the system may allow for simultaneous irradiation of sample material and measuring the emitted NQR signal frequency of the sample material.

In another aspect, the invention may provide a system and method of utilizing NQR to detect explosive material using an RF power level safe for human scanning and testing. The system may optimize power consumption through the continuous wave irradiation signals at targeted frequencies to operate effectively in scanning a human potentially carrying an explosive or target molecule with up to 1 W of power. The embodiment may provide a method for exciting a target molecule at a lower power (a power safe for human exposure) while still effectively measuring the NQR emission. Further, this low amount of power, safe for human exposure, would allow for detection of target material being carried within a human body or cavity.

In one aspect, an embodiment of the invention may provide a method for the remote detection of explosives by Nuclear Quadrupole Resonance comprising the step of using a scan scheduler broadcasting different frequencies to the sample test material and correlating the return frequencies with a library of known returns.

In another aspect, an embodiment of the invention may provide a method for the remote detection of explosives by Nuclear Quadrupole Resonance comprising the step of avoiding false alarms or false positives by conducting multiple detection tests within a frequency range, rather than just at one frequency.

Another aspect of an embodiment may provide a method for the remote detection of explosives by Nuclear Quadrupole Resonance measurements comprising the step of increasing a dwell time by lengthening the time a sample material, or the material under test, is exposed to the radiation excitation frequency. Another step may comprise utilizing frequency generation and probing the material under test a number of times for a give frequency.

In one aspect, an embodiment of the present invention may provide a method for remotely detecting explosives by Nuclear Quadrupole Resonance comprising the step of monitoring the total power output from multiple signal generators so the total power output across all the signal generators does not exceed a predetermined safety level of about 1 watt.

BRIEF DESCRIPTION OF THE SEVERAL VIEWS OF THE DRAWINGS

A sample embodiment of the invention, illustrative of the best mode in which Applicant contemplates applying the principles, is set forth in the following description, is shown in the drawings and is particularly and distinctly pointed out and set forth in the appended claims.

Similar numbers refer to similar parts throughout the drawings.

DETAILED DESCRIPTION

This application is related and an improvement upon U.S. application Ser. No. 12/957,820 filed Dec. 1, 2010; Ser. No. 12/957,843 filed Dec. 1, 2010; Ser. No. 12/957,859 filed Dec. 1, 2010; Ser. No. 12/957,893 filed Dec. 1, 2010; 61/676,495 filed Jul. 27, 2012; and 61/676,506 filed Jul. 27, 2012, all of which are incorporated herein by reference.

Figure 1:
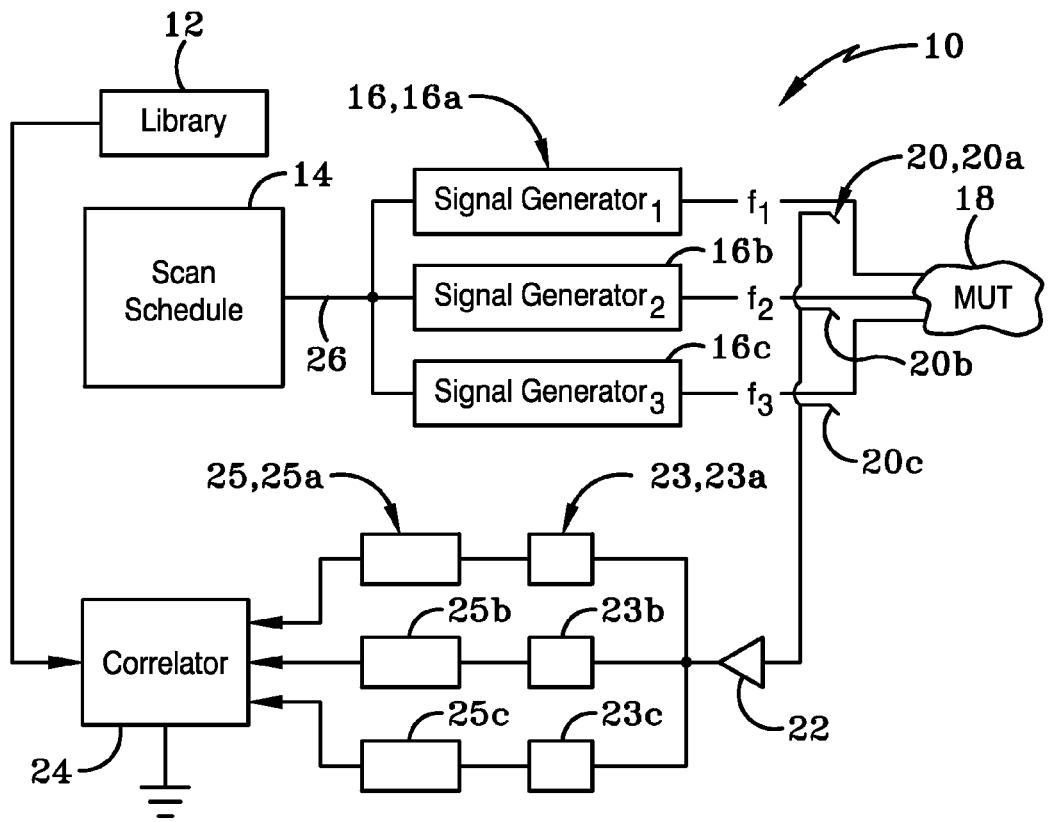
FIG. 1 is a diagrammatic view of a measurement system configured to perform an embodiment of the method of the present invention for remotely detecting a target material within a sample material using Nuclear Quadrupole Resonance.

Referring to FIG. 1, a system 10 is configured to operate and perform an embodiment of the present invention of a method for remotely detecting explosives or target materials/molecules 30 (FIG. 2) using measured NQR emissions. The system comprises a library of known material frequencies 12, a scan schedule 14, a signal generator 16 containing, sample material or Material Under Test (MUT) 18, a directional coupler 20, an amplifier 22, and a correlator 24. Scan schedule 14 is in communication with signal generator 16 via a cable line 26. Directional coupler 20 permits NQR emissions from sample material 18 to be sent through amplifier 22, filter 23, receiver 25 to correlator 24 via transmission lines (unnumbered). Library 12 is operatively connected to correlator 24. System 10 includes multiple probes (not shown) operating each at different excitation frequencies within the measurement chamber (not shown) where the MUT 18 is placed. The NQR emissions from the MUT 18 coupled to the individual probes are received and their frequencies are correlated with those known frequencies of target substances within the library.

In accordance with an aspect of the present invention as herein described above, the system 10 transmits or Irradiates a continuous wave signal through a probe into sample material 18 which is inside a measurement chamber, which could generate an NQR emission from the sample material 18. System 10 allows for simultaneous irradiation of sample material and measurement of the NQR emissions from the sample material 18.

In accordance with another aspect of the present invention, CW system 10 has a reduced relaxation time over previous NQR detection systems utilizing irradiation pulses. This is because conventional pulsed systems irradiate a sample material, then the pulses must be turned off so the pulsed system can "listen" for an NQR return response. The relaxation time is the time period between when the signal generator is turned off to when a return frequency of the sample material has stopped resonating. The sample material cannot be excited again until it has stopped resonating. For TNT, this time is about 8 seconds in a conventional pulsed NQR detection system. The continuous irradiation wave in system 10 created by signal generator 16 does not require the long relaxation time ordinarily needed for a pulsed system and system 10 can measure or "listen" for an NQR response while sending out continuous wave irradiation signals. System 10 has a relaxation time in a range from about 1 millisecond to about 10 milliseconds. System 10 further provides an improved signal-to-noise ratio over the conventionally known pulsed systems by transmitting or irradiating only desired signal frequencies into the sample material 18, rather than in a pulsed system which broadcasts or transmits energy into a great number of frequencies into a sample material.

In accordance with another aspect of the present invention the system 10 provides for a continuous wave signal to generate an NQR response return frequency within the sample material under test wherein the dynamic range is approximately from about −120 db to about −150 db. Dynamic range is an absolute value representing the range of values, in decibels, of the broadcast signal strength to the return frequency signal strength.

In operation, the signal generator 16 sends a continuous wave RF signal into the sample material 18. Signal Generator 16 is a RF signal generators capable of producing CW (continuous wave) signal. The output frequency can usually be tuned anywhere in the frequency range of the generator. The bridge circuit, such as the one disclosed in the related and co-owned U.S. Application titled "NUCLEAR QUADRUPOLE RESONANCE SYSTEM" filed contemporaneously herewith on equal date as this application, and is incorporated herein as if fully rewritten. The bridge circuit is usually incorporated between the generator and the probe exciting the MUT to provide a means to cancel the transmitted signal so as not to interfere with the receiver listening for the NQR emissions from the MUT.

The signal generator 16 is a single unit capable of broadcasting or transmitting a frequency. As shown in FIG. 1 as 16a, 16b, and 16c, three signal generators broadcast a different continuous wave frequency into the sample material 18. The three signal generators 16a, 16b, 16c, output a first frequency $f_1$, a second frequency $f_2$, and a third frequency $f_3$ respectively. A majority of explosives contained in sample material 18 have NQR frequencies in the range from about 200 kHz to about 25 MHz. Accordingly, signal generator 16 must be able to broadcast input signals in this range from about 200 kHz to about 25 MHz.

Then, sample material 18 returns a NQR resonance FID or first return frequency signal to through directional the respective directional coupler 20a, 20b, 20c. Couplers 20a, 20b, 20c send return signal through amplifier 22. Each respective return signal is filtered 23a, 23b, 23c where it is received by a respective receiver 25a 25b, 25c. Unlike conventional pulsed systems, the return signal is integrated into each respective receiver 25a 25b, 25c. The return signal is sent from receivers 25a, 25b, 25c to correlator 24.

Scan schedule 14 is in electrical communication with signal generator 16. Scan schedule 14 may be an electronic device having a processor (not shown) to transform or preform logic and may be programmed by a user. Scan schedule 14 communicates with signal generator 16, so generator 16 can irradiate sample material 18 with energy at different frequencies. Further, scan schedule 14 may be programmed to allow for different frequencies to be broadcasted by the signal generator 16 into the sample material at different times, rather than all at once. Scan scheduler 14 is programmed to provide a scan schedule that avoids resonant lines or frequencies at which closely adjacent 28 (FIG. 2) or identical spectral lines exist between a target molecule 30 (FIG. 2; i.e., nitrogen bonds in an explosive or contraband) and a benign material 32 (FIG. 2).

Figure 2:
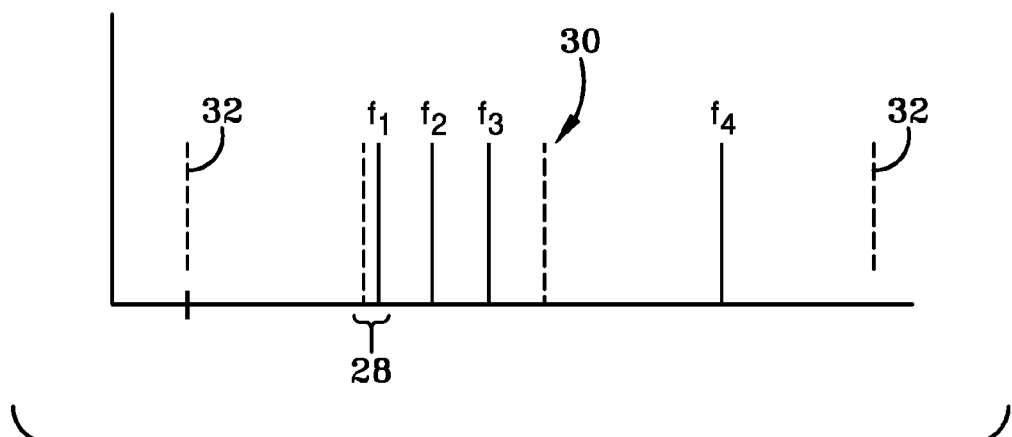
FIG. 2 is an exemplary diagram of spectral lines of NQR emissions, wherein a scan schedule to look for multiple NQR frequencies avoids closely adjacent spectral lines of the target material and benign materials in an attempt to more quickly identify the target material according to one embodiment of the present invention.

As shown in FIG. 2, one embodiment of the system 10 provides, the scan scheduler 10 causing generator 16 to output four frequencies, f1, f2, f3, f4, in an attempt to locate the target molecule 30. Scan scheduler 14 purposefully avoids any benign molecules 32 and close spectral lines 28. For example, if a target molecule 30 (i.e., an element of an explosive or contraband) resonates at a known frequency and a benign material 32 is known to exist within the sample material 18 having the same frequency as the target molecule 30, then scan schedule 14 does not schedule an irradiation signal to be broadcasted by generator 16 at that frequency because it would yield an ambiguous result. System 10 generates signals that avoid known ambiguities between target molecules 30 and benign materials 32 to avoid ambiguous results or false positives.

As noted in the background of this specification, in previous methods of utilizing NQR to detect the presence of a molecule, energy would be pumped in pulses to closely adjacent the top of one of the spectral lines. Then, the energy coming back at the same frequency (FID or return frequency) would indicate a positive result.

An embodiment of the present invention creates a scan schedule 14 to cover those unique places where the target molecules 30 are likely to exist away from or not near any benign molecules 32. The amount of power expected to be used to locate the target molecules 30 allows a programmer to estimate the amount of time the sample material 18 must be irradiated. The scan schedule 14 is programmed based on this estimation so as to be able to obtain enough processing gain. Scan schedule 14 communicates with signal generator 16 to broadcast a particular frequency at a predetermined power level for a predetermined length of time.

Scan schedule 14 can simultaneously set a desired continuous wave irradiation frequency signal and power level. The continuous wave signals from generator 16 permits system 10 to broadcast signals into sample material 18 while simultaneously listening for the return frequency (FID). This greatly reduces relaxation time in system 10. It is contemplated that relaxation times for system 10 will be in the range from about 1 millisecond to about 10 milliseconds. Recall, in conventional pulsed NQR systems a relaxation time for locating TNT explosives can be upwards of eight seconds.

The relaxation time is reduced because when the continuous wave signal irradiates into the sample material 18, the excited sample material 18 resonates at an Immediately measurable frequency. Material 18 remains at that resonating frequency because it is being continuously excited by continuous wave from generator 16. Whereas, the conventional pulsed NQR systems send a pulse or burst of signal to excite the sample material. The sample material does not remain at a constant return resonating frequency because it is not being continuously excited. Thus, in a conventional pulsed system, one must wait until the sample material stops resonating until it can be excited again with another pulse. Thus, the conventional pulsed system has a relaxation time of around eight seconds for TNT.

Figure 4:
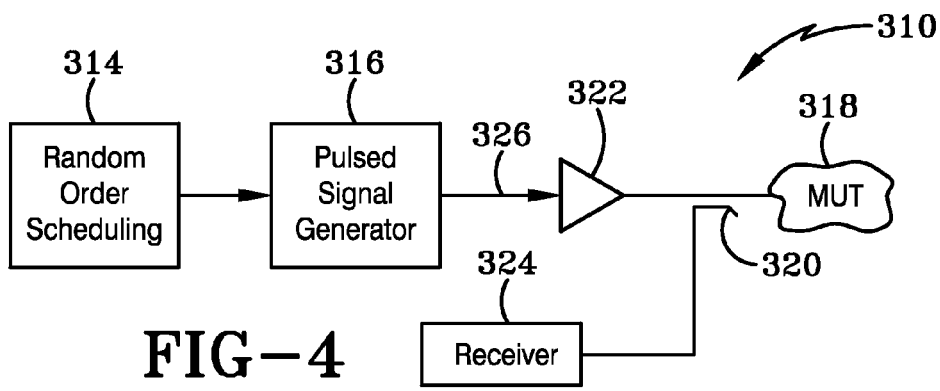
FIG. 4 is a diagrammatic view of a third system configured to perform an alternative embodiment of the method of the present invention.

Additionally, scan schedule 14 may also be programmed to provide randomly broadcasted frequencies at randomly selected power levels for a random length of time (See FIG. 4). Or, scan schedule 14 may be programmed to be semi-random having randomly broadcasted frequencies at randomly selected power levels for a random length of time and predetermined frequencies and power levels for a set time. The advantage of the semi-random scan schedule is to confuse or make it more difficult for an opponent who may be listening into the frequency broadcast. This is a countermeasure that does not allow an opponent to detect the purpose of the system 10. Further, this counter-measure of a semi-random scan schedule makes it very difficult for an opponent to jam a machine or system 10, even if the opponent understands the machine's operation because of the semi-random broadcast frequencies.

Further, scan schedule 14 may be programmed to implement a stepwise correlation progress algorithm. A search tree approach may be implemented to locate a target molecule 30 in the sample material 18. The search tree approach permits signal generator 16 to broadcast a first irradiation signal into the sample material under test 18. Sample material 18 returns a FID or first return frequency signal to the correlator 24. If correlator 24 determines (correlator 24 determination sequence described below) the first return signal is not from a target molecule 30, schedule 14 will cause signal generator 16 to broadcast a second irradiation signal, not equal to the first irradiation signal, into the sample material 18. This process repeats until a target molecule 30 has been located by correlator 24 or all frequencies in a predetermined range have been broadcasted into the sample material 18.

An exemplary process of the search tree approach provides a first irradiation signal generated and broadcasted into the sample material 18 at about 5.6 MHz. If correlator 24 does not indicate the first signal located a target material 30, a second irradiation signal at about 3.2 MHz is generated and broadcasted into the sample material 18. Alternatively, the search tree approach may broadcast a plurality of irradiation signals into the sample material 18 at one time. For example, two signals, about 5.6 MHz and about 3.2 MHz may be simultaneously broadcasted into the sample material 18. Correlator 24 first determines whether the first signal of 5.6 MHz locate a target material 30. If the first irradiation signal does not locate a target material 30, correlator 24 immediately determines if the 3.2 MHz second signal located any target molecule 30, thereby speeding up the scanning process. For the purposes of this description, the two signal frequencies 5.6 MHz and 3.2 MHz are not intended to be limiting and may be different frequencies to locate a desired target material. Further, one advantage of utilizing the stepwise correlation progress algorithm is that system 10 does not have to scan as many frequency slots. This results in a shorter time period that the sample material 18 has to be in a test chamber or subject to irradiation test signals. Thus, using the stepwise correlation progress algorithm, system 10 can detect sample material 18 as a person walks through a portal or down a short hallway.

Library 12 (FIG. 1) comprises a list of all of the possible materials that could exist in a test space containing the sample material. A frequency response of material frequency and power response is further stored in library 12. More particularly, library 12 houses and carries the spectral signatures of many types of target molecules 30 (i.e., explosives and contraband). Preferably, library 12 operates via logic and is housed and electronically stored within a computer system having a processor (not shown).

Library 12 is in communication with and sends electrical signals to correlator 24. Correlator 24 (FIG. 1) is preferably hardware-implemented and comprises logic to determine whether a sample material 18 return frequency matches a frequency from the library 12. Library is populated with a list of known excitation frequencies of known target materials. For example, a certain explosive may have a first excitation frequency around 200 kHz. Then, this explosive could have a second excitation frequency around 1 MHz, and so on. These excitation frequencies for each respective explosive target material would be keyed into the library so the correlator 24 may determine if the return frequencies observed from the material under test 18 contain a target material.

Correlator 24 correlates the raw return sample material frequency with data from the library 12. If there is a high correlation between correlator received return frequency data and the library data, a microcontroller (not shown) may be used to drive memory card event log (not shown) and also provide an operator interface alarm condition indicator (not shown).

It is the purpose of the library 12 and the correlator 24 to select out those resonances that do not normally occur in both the target 30 and the benign materials 32. Therefore, one can both eliminate spectral sensing for those resonances that are identical or closely identical to the target molecule 30.

"Logic", as used herein, includes but is not limited to hardware, firmware, software and/or combinations of each to perform a function(s) or an action(s), and/or to cause a function or action from another logic, method, and/or system. For example, based on a desired application or needs, logic may include a software controlled microprocessor, discrete logic like a processor (e.g., microprocessor), an application specific integrated circuit (ASIC), a programmed logic device, a memory device containing instructions, and electronic device having a processor to perform logic or the like. Logic may include one or more gates, combinations of gates, or other circuit components. Logic may also be fully embodied as software. Where multiple logics are described, it may be possible to incorporate the multiple logics into one physical logic. Similarly, where a single logic is described, it may be possible to distribute that single logic between multiple physical logics.

Figure 3:
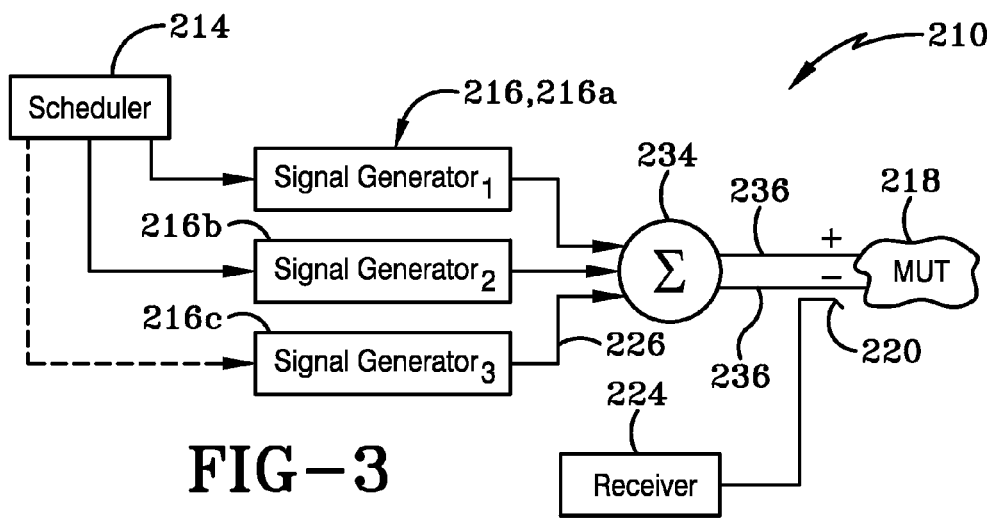
FIG. 3 is a diagrammatic view of a second system configured to perform an alternative embodiment of the method of the present invention.

As shown in FIG. 3, a second embodiment system 210 may include a scan schedule 214, a signal generator 216, sample material 218, a directional coupler 220, a receiver 224, transmission lines 226, a mixer or diplexor 234, and twin lead lines 236. Scheduler 214 is in communication with generator 216. As shown in FIG. 3, generator 216 can be furcated into multiple generators, shown as 216a, 216b, and 216c, respectively, each able to broadcast a continuous wave irradiation signal at a given frequency. These three signals are carried via transmission lines 226 to mixer 234 and broadcasted to material 218 via twin lead lines 236. Return frequencies are transmitted through the directional coupler 220 to a receiver 224. Receiver 224 is preferably a twenty-bit receiver having a dynamic range receiving capacity between about 0 to about 90 db. In this system, the multiple excitation frequencies are directly coupled to a single probe within the measurement chamber. NQR emissions from the MUT are coupled to a receiver with the necessary selectivity to view the separate frequencies.

In system 210, an additional signal is purposefully generated to have a frequency not adjacent a target molecule 30. As shown in FIG. 3, scan schedule 214 cause generator 216c to generate this third signal purposefully far away from target material 30 (FIG. 2) spectral line. This additional third signal from generator 216c minimizes false alarms or false positives results by looking at additional information that was not necessary to the original determination of the target material 30. The third signal should be quiet (i.e., not yielding any return frequency from a target material) at this "far away" frequency. The term "far away" refers to a frequency that is not adjacent the frequency of the target molecule. This confirms the location and presence of target material 30 in sample material 18 from signals broadcasted by generators 216a, 216b. Further, the term third signal is not intended to be limiting, clearly it could be any numbered derivative broadcasting an additional signal.

As shown in FIG. 4, a third embodiment system 310 to detect explosives using NQR includes a random scan scheduler 314, a pulsed signal generator 316, sample material 318, a directional coupler, an amplifier 322 and a receiver 324. Signals are transmitted through transmission lines 326 through amplifier 322 and broadcasted into sample material 318. Return frequencies are transmitted through the directional coupler 220 to a receiver 224. The scheduler that controls the frequencies and pulses transmitted by the signal generator selects the frequencies rather randomly to prevent an independent observer that might be monitoring the test frequencies and their sequence of transmission pulses from being recorded for later application of countermeasures to prevent the system from detecting the targeted material in the MUT or simply by selecting a material that is not being checked for on that particular day for expediency purposes.

Rather than providing a continuous wave irradiation signal as the first two embodiments 10, 210 of the present invention, system 310 provides pulsed RF irradiation signal at random intervals and random frequencies for random time periods. As a general rule, "dwell time" is the amount of time one has to dwell on the target material, or amount of time the target material is subjected to irradiation signal. Dwell time is ordinarily the inverse of the particular bandwidth involved. With reference to pulsed system 310, false positive results may be reduced by increasing the dwell time. Dwell time is increased by either increasing the amount of time that the material under test 18 is subjected to the radiation or, in a stepped system by coming back to the same frequency multiple times so that when a number of positive results occur over time it can be uniquely determined that the target molecule is present.

With continued reference to the increased dwell time in system 310, the result is that the signal-to-noise ratio and the false alarm rate can be improved by increasing the amount of dwell time that one spends at one frequency. When a plurality of frequencies are generated, for instance by an arbitrary or random schedule 314 sent to generator 316, then it is possible to revisit a particular frequency of interest, for example as many as 50 times. This would yield 50 positive test results of the presence of the target molecule, resulting in a high degree of confidence that the target material 30 (FIG. 2) is present in the sample 18.

In order to avoid detection so as to prevent counter measuring, the scheduler 314 (FIG. 4) may schedule the waveforms in random fashion, it being important that a particularly known resonant frequency (i.e., a frequency of an explosive or contraband) be visited a number of times to provide a reliable result.

Figure 5:
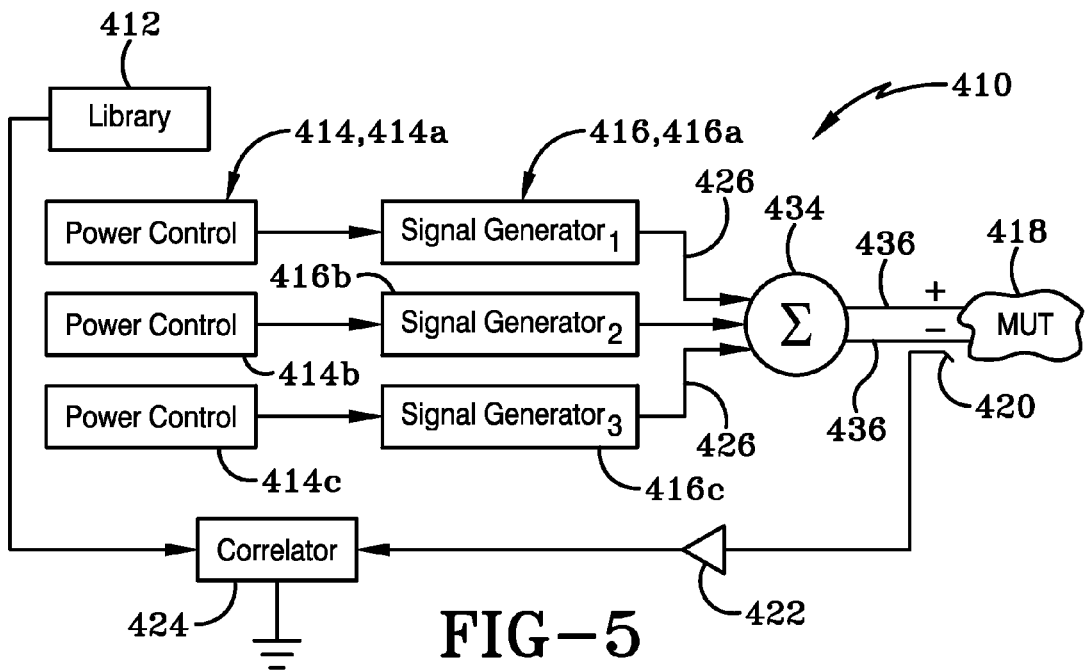
FIG. 5 is a diagrammatic view of a fourth system similar to FIG. 3 configured to perform an alternative embodiment of the method of the present invention but with an ability to control the power levels of the signal generators.

With primary reference to FIG. 5, a fourth embodiment system 410 includes a library 412, a power control 414, a signal generator 416, sample material 418, a directional coupler 420, an amplifier 422, a correlator 424, transmission lines 426, a mixer or diplexer 434 for transmitting signals via twin leads 436 to sample material 418. As shown in FIG. 5, power control may be separated into individual control units 414a, 414b, and 414c connected to first signal generator 416a, second signal generator 416b, and third signal generator 416c, respectively. Generators 416a-c transmit signals to mixer 434 for transmitting signals via twin leads 436 to sample material 418. Directional coupler 420 permits return signals from sample material 418 to be sent through amplifier 422 to correlator 424 via transmission lines 426. Library 412 is operatively connected to correlator 424.

In accordance with another aspect of the invention as herein described above, the system 410 provides a system using NQR to detect explosive material having using a power safe for human scanning and testing. For further background, a conventional pulse system utilizing a multi-signal generator requires a minimum amount of power for each signal generator. So for example, if 5 watts of power are required to generate a frequency from a conventional pulsed signal generator, then to generate six simultaneous frequencies, 30 watts of total power are needed to irradiate the sample material in an attempt to locate a target molecule. When power wattages begin to increase beyond a few watts of total power, conventional pulse systems are unsafe for human exposure. Typically, conventionally known pulsed NQR systems operate in the range of 1 kW to about 5 kW and are only safe for non-human use as they are used to scan baggage at airports. These unsafe conventional pulsed systems are effectively a type of "microwave oven."

System 410 obviates the increased power ordinarily needed for a conventional system as described above, thus allowing system 410 to be safe for human exposure. System 410 optimizes power consumption through the continuous wave irradiation signals at targeted frequencies. This allows system 410 to operate effectively in scanning a human potentially carrying an explosive or target molecule with less than about 1 W of power. A preferred embodiment of system 410 operates with 10 mW or less. In some instances, it may remain safe to exceed slightly more than 1 W of power for human exposure, those instances are determined by body-mass of a human and should follow acceptable FCC guidelines.

System 410 is safe for human exposure because the amount of power being broadcasted as an electric field is of a minimal amount and can be safely absorbed by a human body. Whereas, the conventional pulsed systems are unsafe and would essentially "cook" any person walking through the electric field of broadcasted frequencies.

If there are certain NQR resonances which are stronger than others for target molecules, then it is possible to detect the target molecules with a reduced amount of power. System 410 chooses only those resonances which have large resonance response and reduce outputs of individual signal generators to those large resonance responses to maintain total power in a safe range for human exposure. The power of simultaneous signal generators in system 410 are adjusted down or their powers are cut when it is determined that target molecules are present in the sample material because robust return resonance is located.

The amount of power in the NQR resonances varies greatly. For example, if three spectral lines and three different materials that exhibited an easily observable return power, then the output power of the signal generators 416 could afford to be cut because system 410 is obtaining enough return power. Thus, system 410 can obtain adequate test results by reducing the power for each frequency generator and still be within the power budget. For those target molecules which have larger return frequencies, the signal-to-noise ratio in detecting these return frequencies is higher. Therefore, system 410 does not need as much irradiating power as a conventional NQR system. With this power cut, system 410 can cover more frequencies and still be within the safe power limit for human exposure.

Additionally, as described herein, NQR resonation frequencies of target materials, like nitrates are temperature dependent. As such, system 10, 210, 310, 410 may provide a thermometer (not shown) or a temperature control system (not shown) in communication with the library and correlator to accurately measure return frequency signals after the sample material has been excited.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 6:
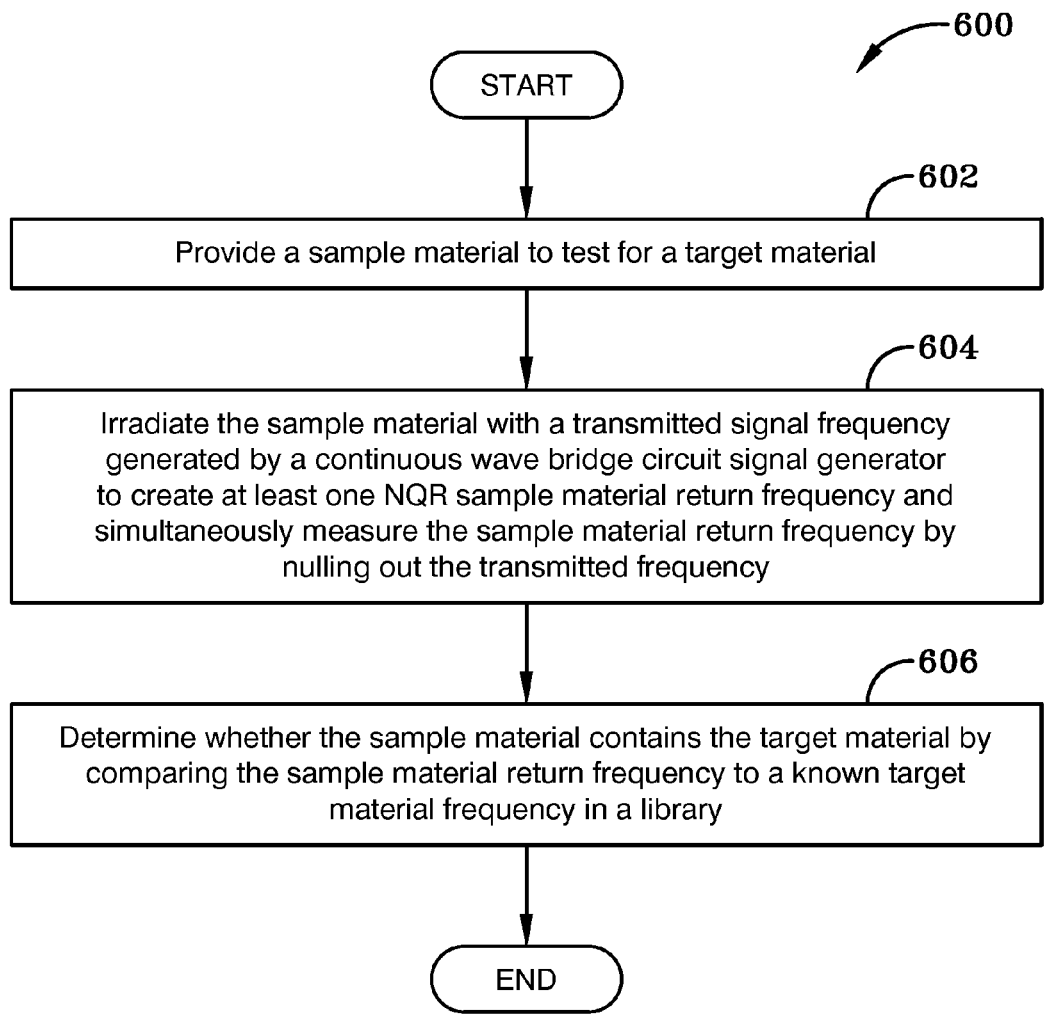
FIG. 6 is a set of method steps according the preferred embodiment of the present invention.

FIG. 6 illustrates a method 600 for detecting explosives using Nuclear Quadrupole Resonance, comprising the steps of providing a sample material to test for a target material 602. Then, irradiating the sample material with a transmitted signal frequency generated by a continuous wave bridge circuit signal generator to create at least one NQR sample material return frequency and simultaneously measuring the sample material return frequency by nulling out the transmitted frequency 604. Then, determining whether the sample material contains the target material by comparing the sample material return frequency to a known target material frequency in a library 606.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the preferred embodiment of the invention are an example and the invention is not limited to the exact details shown or described.

The invention claimed is:

1. A method for detecting target materials using Nuclear Quadrupole Resonance (NQR), comprising the steps of:
   providing a sample material to test for a target material;
   irradiating the sample material with a continuous wave signal to create at least one NQR emission from the sample material and simultaneously measuring the other NQR emissions at different frequencies; and determining whether the sample material contains the target material by comparing the NQR frequencies of the sample material emissions to a known target material frequency in a library;

wherein the step of irradiating the sample material comprises:

creating a step wise search tree scan schedule, the search tree scan schedule configured to irradiate the target material with two different signal frequencies at a first search level, if a first material NQR return frequency is not equal to the target material NQR frequency, then the tree schedule detects a second material NQR return frequency, the tree scan schedule repeating until all material frequencies have been scanned; and irradiating the sample material in accordance with the tree scan schedule.

2. The method of claim 1, wherein the step measuring the sample material return frequency comprises the steps of:
scanning the sample material return frequency within a scan cycle having a time period; and
avoiding NQR return frequencies of known non-target materials to shorten the scan cycle.

3. The method of claim 1, further comprising the steps of:
providing at least one target material NQR frequency in the library;
creating a scan schedule, the schedule including a portion, but not all, of the known frequencies from the library; and
irradiating the sample material in a time period in accordance with the scan schedule to reduce the amount of time necessary to find and identify the target material.

4. The method of claim 1, further comprising the steps of:
providing at least one target material NQR frequency in the library;
creating a scan schedule that includes the target material NQR frequency;
creating a power schedule for identifying the amount of power required to observe the target material NQR frequency; and
irradiating the sample material in accordance with the scan schedule and the power schedule to locate the target material and have enough power for a processing gain.

5. The method of claim 1, wherein the step of irradiating the sample material comprises the steps of:
creating a scan schedule, the scan schedule including a set of randomized frequencies;
irradiating the sample material in accordance with the scan schedule having the randomized set of frequencies to prevent detection of the scanning process by an independent observer.

6. The method of claim 1, wherein the step of creating a search tree scan schedule comprises the step of utilizing an electronic device having a correlation algorithm to create the search tree scan schedule.

7. The method of claim 1, wherein the step of determining whether the sample material contains the target material comprises the steps of:
providing an electronic device having a processor to transform and store correlation logic; and
correlating return sample material frequency with data from the library.

8. The method of claim 1, wherein the step of irradiating the sample material and the step of measuring the NQR emission frequency occur simultaneously.

9. The method of claim 1, wherein the step of irradiating the sample material comprises the steps:
irradiating the sample material with a first irradiating signal frequency;
comparing the sample material return frequency with a known resonance match of the target material frequency; and
irradiating the sample material a second time with a second irradiating signal frequency unequal to the first irradiating signal frequency to minimize a false-positive result.

10. The method of claim 9, further comprising the step of confirming that the first irradiating frequency was correct when a target material is quiet at the second irradiating frequency.

11. The method of claim 1, having a relaxation time in a range from about 1 millisecond to about 50 milliseconds.

12. The method of claim 1, wherein the step of irradiating the sample material further comprises the step of:
powering the signal generator with approximately no more than one watt.

13. The method of claim 1, further comprising the steps of:
increasing a dwell time and measuring multiple frequencies to reduce a number of false positive results.

14. The method of claim 13, wherein the step of increasing the dwell time comprises repeating an irradiation frequency more than one time so a plurality of positive results occurs over a time period to determine the target material is present.

15. The method of claim 1, wherein the sample material is irradiated at the transmitted signal frequency from about 25 to about 75 times.

16. The method of claim 1, further comprising the steps of:
scheduling a continuous waveform signal, generated by the signal generator, in a random frequency arrangement; and
observing a predetermined NQR frequency a set number of times to provide a reliable result.

17. The method of claim 1, wherein prior to the step of irradiating the sample material comprises the step of providing a plurality of irradiating signal generators.

18. The method of claim 17, wherein the step of providing a plurality of signal generator comprises the steps of:
determining an amount of power needed to identify a target material frequency;
monitoring a power output level of each signal generator, each signal generator outputting a different frequency;
reducing the total power output of the signal generators when the target material produces an identifiable resonance.

19. A method for detecting target materials using Nuclear Quadrupole Resonance (NQR), comprising the steps of:
generating a continuous wave signal in a signal generator;
transmitting the continuous wave signal into a sample material; and
observing an NQR emission from the sample material by coupling NQR signals to the receivers via directional coupler;
wherein the step of transmitting the continuous wave signal into the sample material comprises:
irradiating the sample material with a first irradiating signal frequency;
comparing the sample material return frequency with a known resonance match of a target material frequency; and irradiating the sample material a second time with a second irradiating signal frequency unequal to the first irradiating signal frequency to minimize a false-positive result.

20. A method for detecting target materials using Nuclear Quadrupole Resonance (NQR), comprising the steps of:

coupling a transmitted signal through a bridge circuit to a probe illuminating a sample material under test (MUT) while listening for at least one NQR emissions that appear across the balanced output terminals of the bridge circuit;

coupling multiple transmitted signals at different frequencies through multiple bridges to drive the probes that illuminated the MUT while listening for the NQR emissions that appear across the bridge terminals using multiple receivers/detectors; and increasing a dwell time and measuring multiple frequencies to reduce a number of false positive results.

\* \* \* \* \*